(12) United States Patent
Komatsu

(10) Patent No.: US 7,435,309 B2
(45) Date of Patent: Oct. 14, 2008

(54) METHOD OF MANUFACTURING SOLID GATHER FORMING MEMBER

(75) Inventor: Yoshihisa Komatsu, Tochigi (JP)

(73) Assignee: Kao Corporation, Tokyo (JP)

( * ) Notice: Subject to any disclaimer, the term of this patent is extended or adjusted under 35 U.S.C. 154(b) by 394 days.

(21) Appl. No.: 10/536,895

(22) PCT Filed: Oct. 3, 2003

(86) PCT No.: PCT/JP03/12731

§ 371 (c)(1),
(2), (4) Date: Oct. 4, 2005

(87) PCT Pub. No.: WO2004/049988

PCT Pub. Date: Jun. 17, 2004

(65) Prior Publication Data

US 2006/0151091 A1 Jul. 13, 2006

(30) Foreign Application Priority Data

Nov. 29, 2002 (JP) .............................. 2002-348980

(51) Int. Cl.
*B65B 37/00* (2006.01)
*A61F 13/15* (2006.01)

(52) U.S. Cl. .............. 156/161; 156/163; 156/164; 156/229; 156/204; 156/227; 156/494; 156/495; 156/459; 156/461; 156/465

(58) Field of Classification Search .............. 156/204, 156/227, 229, 160, 161, 163, 164, 494, 495, 156/459, 461, 465
See application file for complete search history.

(56) References Cited

U.S. PATENT DOCUMENTS

| 4,488,927 | A | * | 12/1984 | Hooper ...................... 156/464 |
| 4,900,384 | A | | 2/1990 | Sanders |
| 5,190,606 | A | * | 3/1993 | Merkatoris et al. .......... 156/164 |
| 5,714,027 | A | * | 2/1998 | Taub ........................ 156/204 |
| 6,562,017 | B1 | * | 5/2003 | Nakaoka et al. ........ 604/385.28 |
| 6,706,029 | B1 | * | 3/2004 | Suzuki et al. ........... 604/385.28 |

FOREIGN PATENT DOCUMENTS

| FR | 2711057 A1 | * | 4/1995 |
| JP | 64-68503 A | | 3/1989 |
| JP | 2003-33391 A | | 2/2003 |
| JP | 2003-136591 A | | 5/2003 |

* cited by examiner

*Primary Examiner*—Jeff H Aftergut
(74) *Attorney, Agent, or Firm*—Birch, Stewart, Kolasch & Birch, LLP.

(57) ABSTRACT

A method of making a standing gather-forming member having a basal wall and first and second overhangs on both sides of the basal wall. Elastic members are disposed in their stretched state on the inner surface of a middle portion of a continuously running strip-shaped sheet. One of side portions extending on both longitudinal sides of the middle portion is Z-folded to cover a part of the width of the middle portion thereby to form the first overhang. The other side portion is then folded inward along the longitudinal direction to cover the part of the middle portion that remains uncovered with the first-mentioned side portion and to overlay the Z-folded portion of the first-mentioned side portion thereby to form the second overhang and the basal wall.

10 Claims, 6 Drawing Sheets

Fig.8
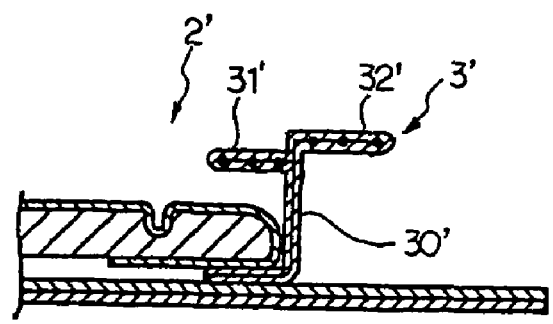
Fig.9(a)  Fig.9(b)  Fig.9(c)
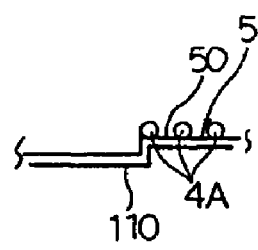 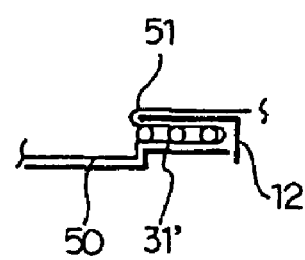 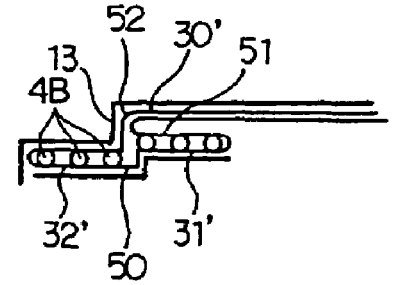

US 7,435,309 B2

METHOD OF MANUFACTURING SOLID GATHER FORMING MEMBER

TECHNICAL FIELD

The present invention relates to a method and apparatus for making a standing gather-forming member used in absorbent articles such as sanitary napkins and incontinence pads.

BACKGROUND ART

JP-A-1-68503 discloses a disposable diaper having a pair of standing gathers outside of the lateral edges of the absorbent member. The standing gathers have a T-shaped cross-section composed of a basal wall and overhangs on both lateral sides of the basal wall. The disposable diaper is adapted to have the upper side of the T-shaped standing gathers applied to the wearer's thighs thereby to prevent leaks.

While nonwoven fabric, etc. with a good hand is used to form such standing gathers, it has been difficult to make the standing gathers continuously and stably because, for one thing, the overhangs are narrow and, for another, a certain height of the basal wall should be secured.

DISCLOSURE OF THE INVENTION

An object of the present invention is to provide a method and apparatus for making a standing gather-forming member, by which a standing gather-forming member providing a snug fit and a reliable protection against leakage is produced continuously and stably.

The present invention accomplishes the above object by providing a method of making a standing gather-forming member having a basal wall and first and second overhangs sticking from the basal wall to both lateral sides. The method includes a first step of forming the first overhang and a second step of forming the second overhang and the basal wall that follows the first step. In the first step, an elastic member is disposed in its stretched state on the inner surface of a middle portion of a continuously running strip-shaped sheet in the longitudinal direction of the middle portion, and one of side portions extending on both longitudinal sides of the middle portion is Z-folded so as to cover a part of the width of the middle portion. In the second step, the other side portion is folded inward along the longitudinal direction so as to cover the part of the middle portion that remains uncovered with the first-mentioned side portion and also overlay the Z-folded portion of the first-mentioned side portion.

The present invention also accomplishes the above object by providing apparatus for making a standing gather-forming member having a basal wall and first and second overhangs laterally extending from the basal wall. The apparatus has a conveying system for conveying along a conveying route a strip-shaped sheet having an elastic member disposed on the middle portion thereof in its stretched state, a first folding unit having a first guide provided on one side of the conveying route so as to narrow the width of the conveying route from that side, and a second folding unit having a second guide provided on the other side of the conveying route so as to narrow the width of the conveying route from the other side. The first guide has an inwardly projecting projection configured to hang over a part of the middle portion on the conveying route. The second guide has an inwardly projecting projection configured to hang over a part of the middle portion.

The projection of the first guide is configured to Z-fold one of side portions extending on both longitudinal sides of the middle portion such that the side portion covers a part of the middle portion to form the first overhang.

The projection of the second guide is configured to fold the other side portion inward along the longitudinal direction such that the other side portion covers the part of the middle portion that remains uncovered with the first-mentioned side portion and also overlay the Z-folded portion of the first-mentioned side portion to form the second overhang and the basal wall.

BRIEF DESCRIPTION OF THE DRAWINGS

FIG. 3(a) and FIG. 3(b) are perspectives schematically illustrating essential parts of the apparatus shown in FIG. 1, in which FIG. 3(a) shows the first folding unit, and FIG. 3(b) shows a second folding unit.

FIG. 4(a) and FIG. 4(b) are schematic plans of the first folding unit of the apparatus shown in FIG. 1, in which FIG. 4(a) illustrates only the unit, and FIG. 4(b) shows how the unit operates.

FIG. 5(a) and FIG. 5(b) are schematic plans of the second folding unit of the apparatus shown in FIG. 1, in which FIG. 5(a) illustrates only the unit, and FIG. 5(b) shows how the unit operates.

FIG. 6(a), FIG. 6(b), FIG. 6(c), and FIG. 6(d) schematically illustrate the procedures involved in an embodiment of the method of producing a standing gather-forming member according to the present invention, in which FIG. 6(a) shows a sheet with elastic members disposed on its middle portion, FIG. 6(b) shows the sheet having its side portion folded in and out (Z-folded) to form a first overhang, FIG. 6(c) shows an adhesive applied to the other side portion, and FIG. 6(d) shows the other side portion folded inward to form a second overhang and a basal wall.

FIG. 8 is a cross-section showing an essential part of a sanitary napkin fabricated using a standing gather-forming member made by apparatus according to another embodiment of the present invention.

FIG. 9(a), FIG. 9(b), and FIG. 9(c) schematically illustrate the procedures involved in another embodiment of the method of making a standing gather-forming member according to the present invention, in which FIG. 9(a) shows a sheet with elastic members disposed on its middle portion, FIG. 9(b) shows a side portion of the sheet Z-folded to form a first overhang, and FIG. 9(c) shows the other side portion folded inward to form a second overhang and a basal wall.

BEST MODE FOR CARRYING OUT THE INVENTION

The present invention will be described based on its preferred embodiments with reference to the accompanying drawings.

Figure 1:
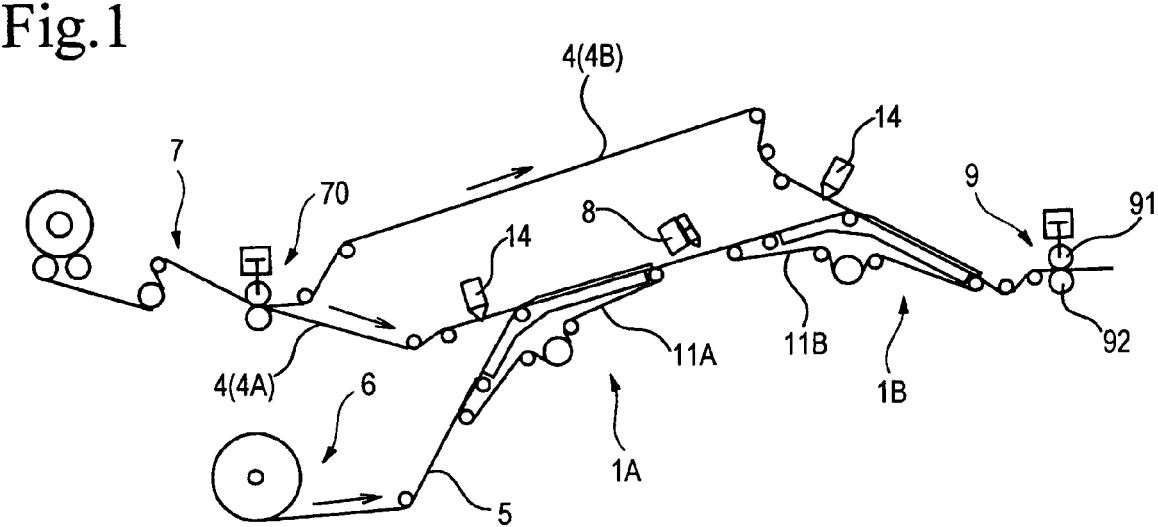
FIG. 1 is a schematic showing an embodiment of the apparatus for producing a standing gather-forming member according to the present invention.

FIG. 1 illustrates an embodiment of the present invention in which apparatus for making a standing gather-forming member (hereinafter simply referred to as "the apparatus") is applied to the production of a standing gather-forming member for use in sanitary napkins. As shown in FIG. 1, the apparatus of the present embodiment has a first folding unit 1A, a second folding unit 1B, a sheet feeder 6, an elastic member feeder 7, an adhesive applicator 8 for bonding both side portions of a sheet, and a pressing unit 9.

Figure 7:
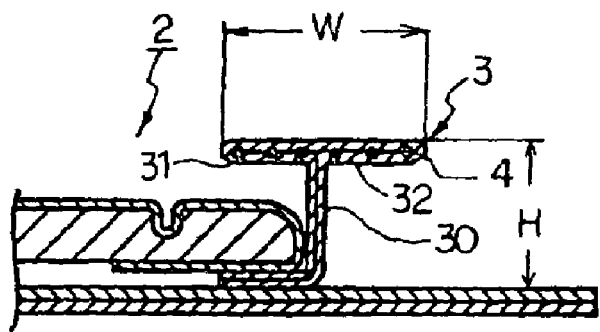
FIG. 7 is a cross-section showing an essential part of a sanitary napkin fabricated using a standing gather-forming member made by the apparatus shown in FIG. 1.

The apparatus of the present embodiment is for making a member providing standing gathers 3 which is used in a sanitary napkin 2 as shown in FIG. 7. A standing gather-forming member made by this apparatus has a basal wall 30, a first overhang 31, and a second overhang 32 extending from the basal wall 30 to the opposing lateral directions to make a substantially T-shaped cross-section. A plurality of elastic members 4 of thread form are arranged in each of the first and the second overhangs 31 and 32. The standing gathers 3 have a height H of 5 to 50 mm and a width W, represented by the distance between the edge of the first overhang 31 and the edge of the second overhang 32, of 6 to 40 mm.

As shown in FIG. 1, the sheet feeder 6 is configured to continuously unwind a continuous strip-shaped sheet 5 from a stock roll and feed the sheet 5 to a conveyor 11A of the first folding unit 1A. The sheet 5 is folded in a prescribed manner in the first folding unit 1A while being carried by the conveyor 11A and then forwarded to a conveyor 11B of the second folding unit 1A, where it is folded in a prescribed manner while being conveyed by the conveyor 11B. The conveyor 11A of the first folding unit 1A and the conveyor 11B of the second folding unit 1B are configured to convey the sheet 5 in that order. A combination of the conveyors 11A and 11B constitutes a conveying system in the apparatus of the invention.

As illustrated in FIGS. 2, 3(a), 4(a), and 4(b), the first folding unit 1A has a conveyor 11A and a first guide 12. The conveyor 11A conveys the strip-shaped sheet 5 along the conveying route R, the sheet 5 having four elastic members 4A disposed on the inner surface of its middle portion 50 in their stretched state. The first guide 12 is provided on one side of the conveying route R so as to narrow the width of the conveying route R from that side. The first guide 12 has an inwardly projecting projection 120 that hangs over a part of the middle portion 50 moving on the conveying route R.

As illustrated in FIGS. 1, 3(b), 5(a), and 5(b), the second folding unit 1B has a conveyor 11B and a second guide 13. The conveyor 11B conveys the strip-shaped sheet 5 along the conveying route R, the sheet 5 having six elastic members 4 disposed on the inner surface of its middle portion 50 in their stretched state. The second guide 13 is provided on the other side of the conveying route R so as to narrow the width of the conveying route R from that side. The second guide 13 has an inwardly projecting projection 130 that hangs over a part of the middle portion 50 on the conveying route R. The six elastic members 4 are the sum of the four elastic members 4A having been arranged on the middle portion while on the conveyer 11A and two additional elastic members 4B arranged on the middle portion while on the conveyor 11B.

Figure 2:
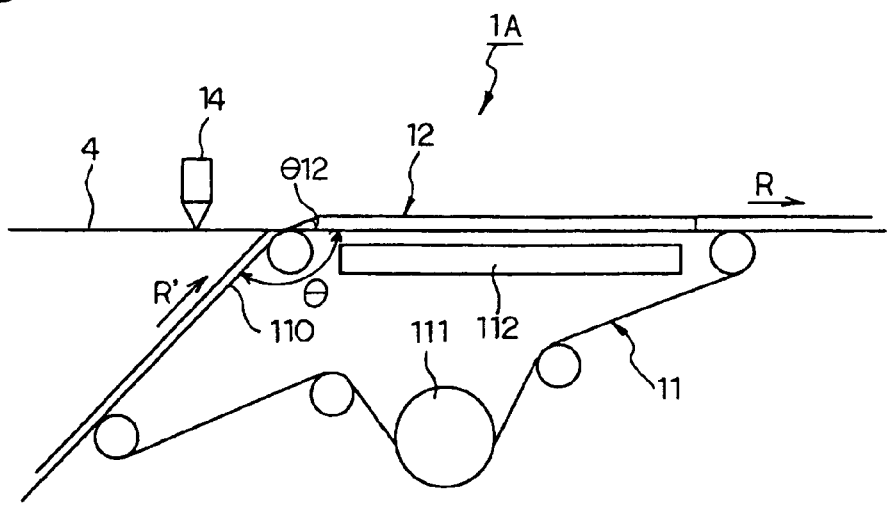
FIG. 2 is a schematic showing a first folding unit in the apparatus of FIG. 1.

As illustrated in FIGS. 1 and 2, the conveyor 11A of the first folding unit 1A and the conveyor 11B of the second folding unit 1B each have an air-permeable endless belt 110 for conveying the sheet 5, a group of rolls including a driving roll 111 driving the belt 110 along the conveying route R, and a vacuum box as a suction mechanism for fixing the middle portion 50 on the belt 110 by suction.

The conveyor belts 110 in the conveyors 11A and 11B are each provided so that the middle portion 50 of the sheet 5 may make a prescribed angle θ between before and after entering the area where the overhang is formed by the first and the second guides 12 and 13. The angle θ is preferably 100° to 150°, more preferably 135° to 145°, from the suction surface of the conveyor, taking the conveying surface as a base. At angles of 100° or greater, the sheet 5 is prevented from failing to be shaped due to sagging. At angles of 150° or smaller, the sheet 5 is prevented from failing to be shaped due to excessive tension.

Figure 3A:
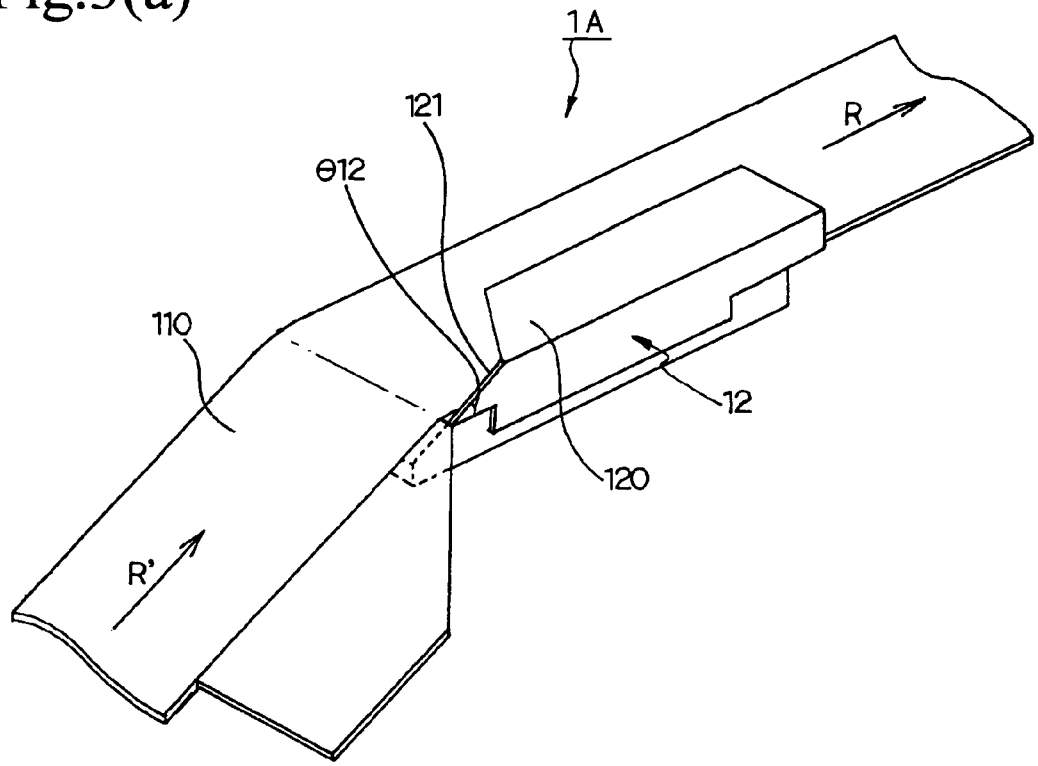
Figure 4A:
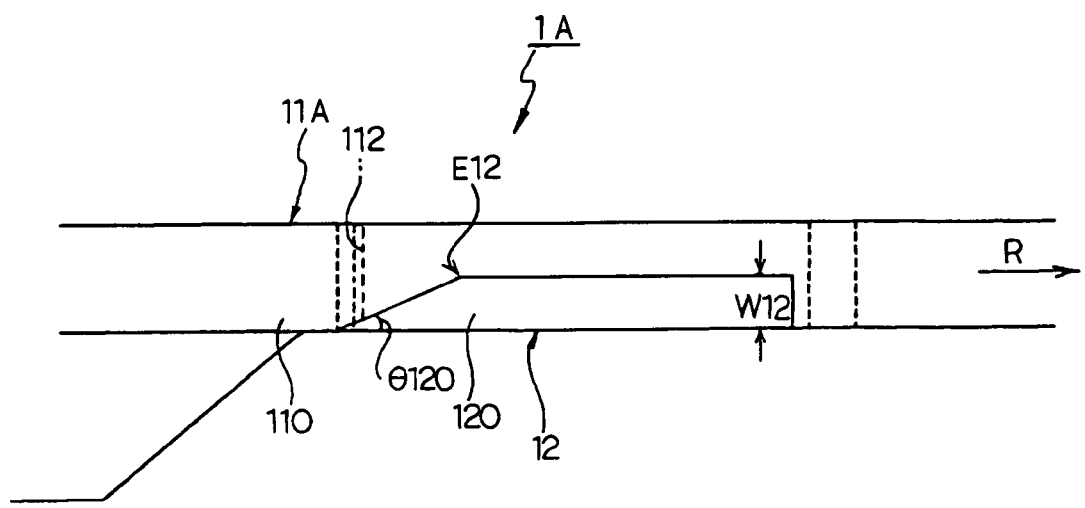
Figure 4B:
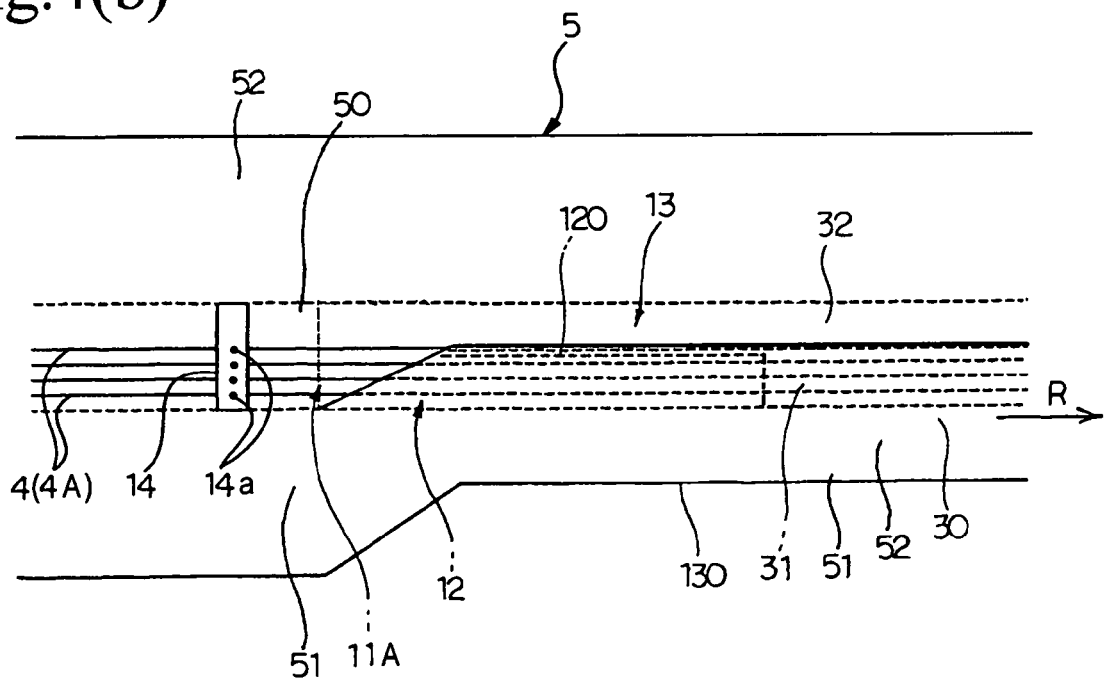

As shown in FIGS. 3(a), 4(a), and 4(b), the projection 120 of the first guide 12 has a trapezoidal shape with its upstream end tapered in its plan view. The projection 120 is designed to Z-fold a side portion 51 located by one side of the middle portion 50 to partly cover the middle portion 50, i.e., to form the first overhang 31.

The upstream end 121 of the first guide 12 rises obliquely. The angle of rise, designated θ12 (see FIG. 3(a)), is preferably 5° to 15°, more preferably 10° to 12°, from the conveying surface. At angles of 5° or greater, the sheet 5 is prevented from failing to be folded. At angles of 15° or smaller, the sheet 5 is prevented from suffering from shaping defects such as wrinkles.

The folding angle θ120 of the upstream taper of the projection 120 of the first guide 12 (the angle from the moving direction of the sheet, see FIG. 4(a)) is preferably 8° to 15°, more preferably 10° to 12°, measured from the outer face of the first guide 12 perpendicular to the conveying route R (hereinafter referred to as "edge face"). At angles of 8° or greater, shaping defects due to the failure of the sheet 5 to be folded is avoided. At angles of 15° or smaller, the sheet is prevented from wrinkling due to the steep rise.

The projecting width W12 of the projection 120 (see FIG. 4(a)) is preferably 8 to 15 mm, more preferably 10 to 12 mm, measured from the edge face of the first guide 12. With widths of 8 mm or greater, the fold width by the first guide is surely reflected in the resulting Z-fold. With widths of 15 mm or smaller, it is easy to control the dimension of the sheet as desired, and shaping defects such as wrinkles are prevented.

Figure 6A:
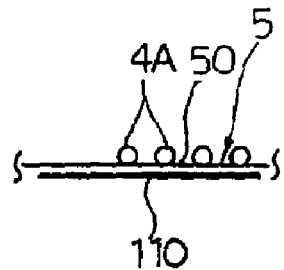
Figure 6B:
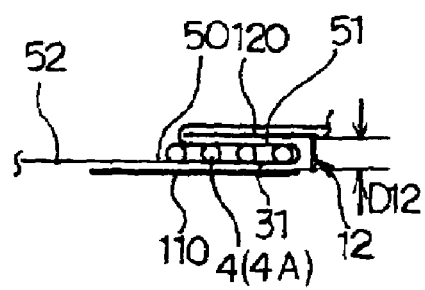
Figure 6C:
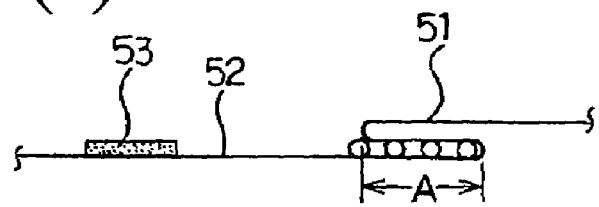

The distance D12 (see FIG. 6(b)) between the lower side of the projection 120 and the upper side of the belt 110 is preferably 1.0 to 2.5 mm, more preferably 1.5 to 2.0 mm, at folding end point E12 (see FIG. 4(a)) of the first guide 12. With distances of 1.0 mm or greater, shaping defects such as wrinkles due to increased resistance of the sheet 5 are avoided. With distances of 2.5 mm or smaller, shaping defects such as wrinkles are prevented.

Figure 3B:
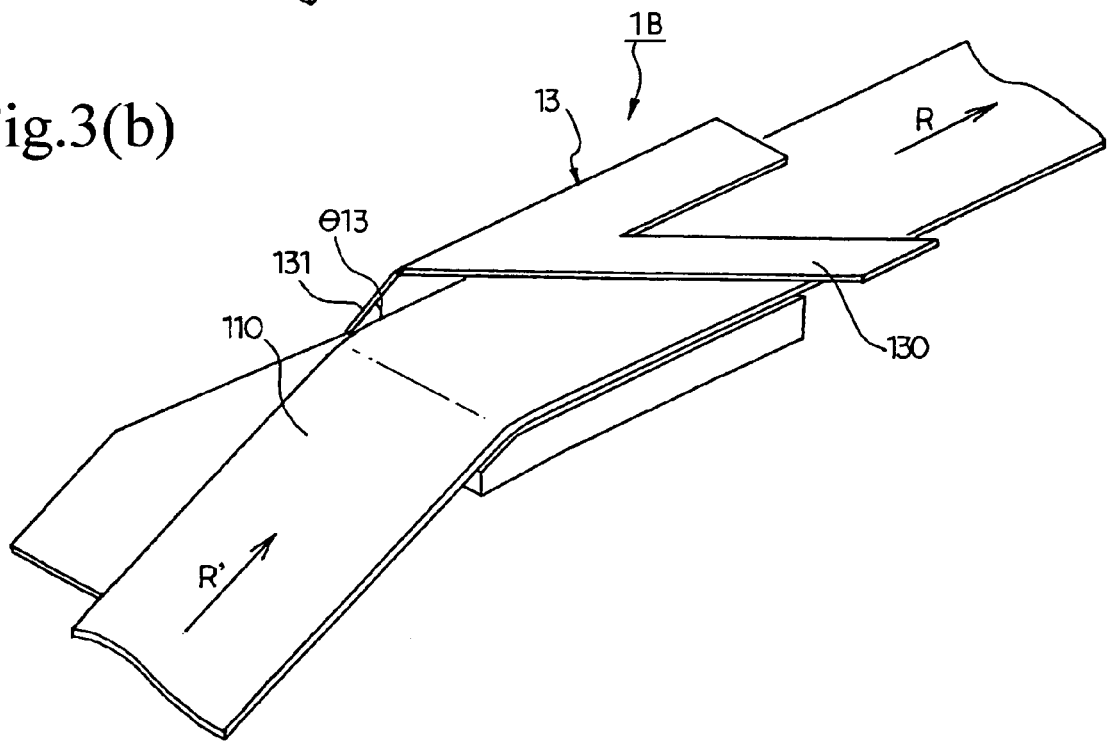
Figure 5A:
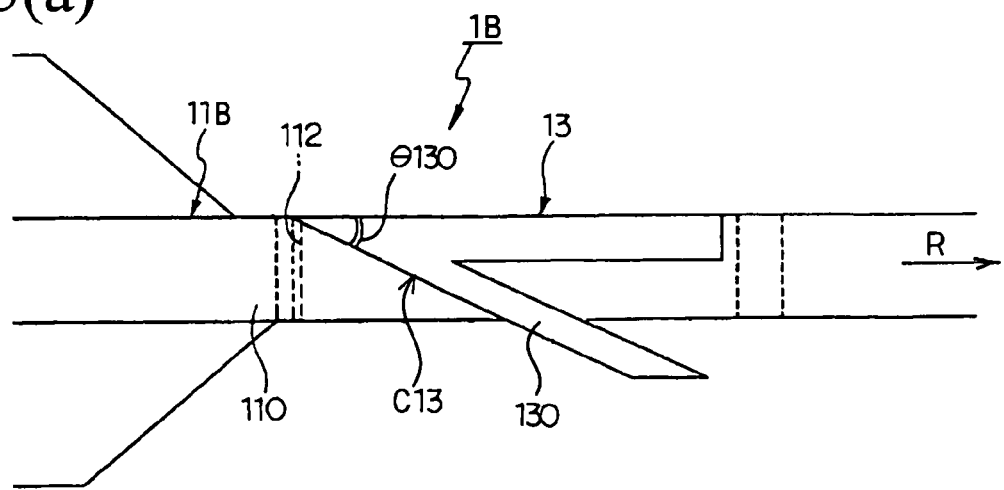
Figure 5B:
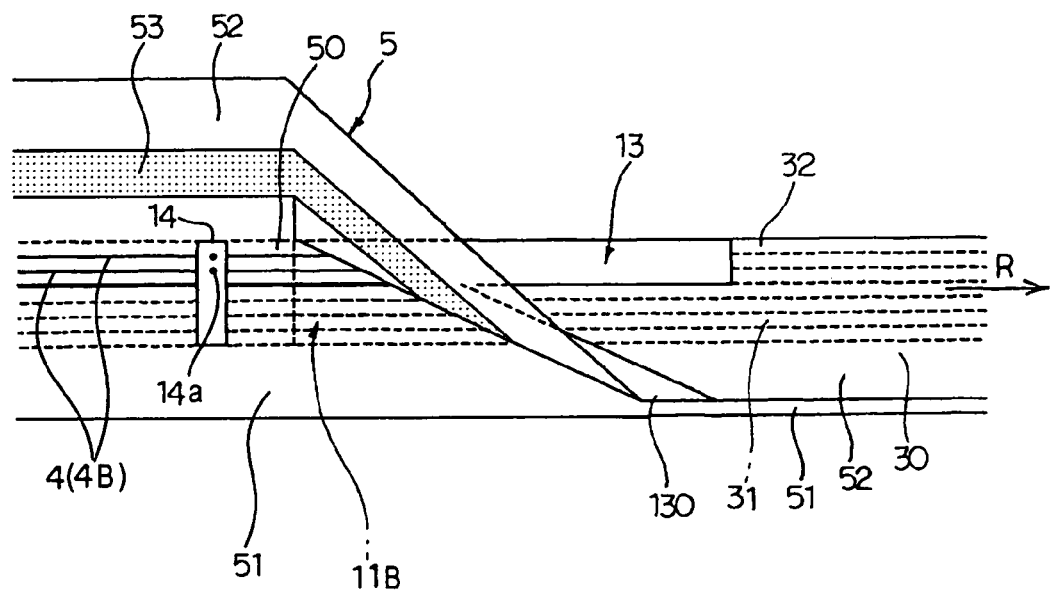

As illustrated in FIGS. 3(b), 5(a), and 5(b), the second guide 13 of the second folding unit 1B is provided on the side of the conveying route R opposite to the side where the first guide 12 is provided so as to narrow the width of the conveying route R from that side. The second guide 13 has an inwardly projecting projection 130 that hangs over a part of the middle portion 50 on the conveying route R. The projection 130 has a V shape across the conveying route R in the plan view.

The projection 130 of the second guide 13 is designed to inwardly fold the side portion 52, which is another one of the side portions located by both sides of the middle portion 50, along the longitudinal direction so as to cover the part of the middle portion 50 that remains uncovered with the side portion 51 and also to overlay the upper side of the Z-folded portion of the side portion 51, thereby to form the second overhang 32 and the basal wall 30.

The upstream end 131 of the second guide 13 rises obliquely. The angle of rise, designated θ13 (see FIG. 3(b)), is preferably 5° to 15°, more preferably 8° to 10°, in view of the fabricability of the material.

The folding angle θ130 of the upstream taper of the projection 130 of the second guide 13 (see FIG. 5(a)) is preferably 5° to 15°, more preferably 8° to 10°, in view of the fabricability into the standing gathers.

Figure 6D:
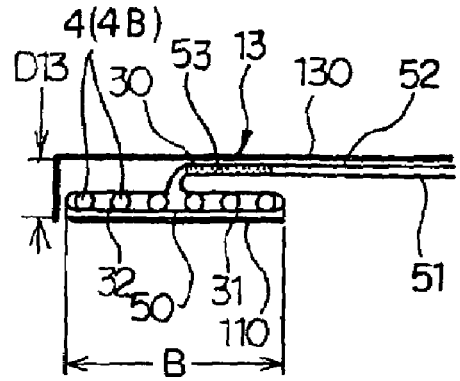

The distance D13 (see FIG. 6(d)) between the lower side of the projection 130 of the second guide 13 and the facing upper side of the belt 110 (conveyor) is larger than the distance D12 (see FIG. 6(*b*)) between the lower side of the projection 120 of the first guide 12 and the facing upper side of the belt 110 (conveyor). Symbol C13 in FIG. 5(*a*) indicates a position in the width direction of the conveying route R, the position corresponding to the folding end point E1 of the first guide 12 (approximately the widthwise mid point). The distance D13 at that point C13 is preferably 1.0 to 2.5 mm, more preferably 1.5 to 2.0 mm, in order to prevent positional deviation in folding and to stabilize the folding operation. It is preferred that the distances D13 and D12 be equal.

As shown in FIG. 1, the first and the second folding units 1A and 1B each have an applicator 14 for applying an adhesive at intervals to the elastic members 4 immediately before being set on the respective conveyors 11A and 11B. Each applicator 14 is equipped with a comb nozzle having orifices for ejecting an adhesive at prescribed spacings corresponding to those of the elastic members 4. As illustrated in FIG. 4(*b*), the applicator 14 of the first folding unit 1A is configured to eject an adhesive from orifices 14a corresponding to the four elastic members 4A and apply the adhesive to the elastic members 4A. The applicator 14 of the second folding unit 1B is configured to eject an adhesive from orifices 14a corresponding to the two elastic members 4B and apply the adhesive to the elastic members 4B as illustrated in FIG. 5(*b*).

As drawn in FIG. 1, the elastic member feeder 7 is configured to continuously feed six elastic members 4 from the stock roll, divide the six elastic members 4 into four elastic members 4A and two elastic members 4B by means of a distributor 70, and arrange the former group of the elastic members 4A on the middle portion 50 moving on the first folding unit 1A and the latter group of the elastic members 4B on the middle portion 50 moving on the second folding unit 1B.

The adhesive applicator 8 for bonding both side portions of the sheet is positioned between the first folding unit 1A and the second folding unit 1B as shown in FIG. 1. The adhesive applicator 8 is configured to apply an adhesive to the side portion 52 at intervals so that the side portions 51 and 52 may be partly joined together when superposed on each other in the second folding unit 1B.

The pressing unit 9 has a pair of nip rolls 91 and 92. The pressing unit 9 is configured to press the standing gather-forming material, after the formation of the first and the second overhangs and the basal wall, between the nip to enhance the adhesion between the elastic members 4 and the sheet 5 and between the two side portions of the sheet 5.

The method of making a standing gather-forming material according to the present invention will then be described based on an embodiment in which the above-described apparatus is used with reference to the drawings.

A strip-shaped sheet 5 is fed onto the conveyor 11A of the first folding unit 1A by means of the sheet feeder 6. As shown in FIG. 4(*b*), the sheet 5 is conveyed along the conveying route R while being sucked to the belt 110 by the vacuum box 112 of the conveyor 11A. Four elastic members 4 are arranged with almost equal spacing in their stretched state on the inner side of the middle portion 50 of the moving sheet 5 (see FIG. 6(*b*)). Before the elastic members 4 are arranged, an adhesive is applied thereto by the applicator 14 so that the elastic members 4 are fixed to the sheet 5 via the adhesive.

The conveying route is narrowed from one side by the guide 12, and the side portion 51 (one of the side portions 51 and 52 extending along both sides of the middle portion 50) is Z-folded by the projection 120 of the guide 12 so as to cover the whole width of the part of the middle portion 50 where the elastic members 4A are disposed. As a result, the first overhang 31 of the standing gathers 3 is formed (see FIG. 6(*b*)).

An adhesive 53 is intermittently applied with the adhesive applicator 8 to a prescribed part of the side portion 52, the other side portion of the two side portions 51 and 52 of the sheet 5 which are to be superposed on each other in the second folding unit 1B hereinafter described (see FIG. 6(*c*)).

Any of various adhesives used in sanitary napkins can be used as adhesive 53 to form the basal wall 30 with no particular restriction. Instead of applying the adhesive 53 to the side portion 51, the adhesive 53 may be applied to the area of the side portion 51 on which the side portion 52 is to be superposed, or the adhesive 53 may be applied to both the side portions 51 and 52.

The folded sheet 5 from the first folding unit 1A is sent to the conveyor 11B of the second folding unit 1B and conveyed as sucked to the belt 110 by the vacuum box (not shown) of the conveyor 11B. Two elastic members 4 are disposed in their stretched state on the inner side of the middle portion 50 of the moving sheet 5 along the longitudinal direction of the middle portion 50 (see FIG. 5(*b*)). Before these elastic members 4B are disposed, an adhesive is applied thereto by the applicator 14 so that the elastic members 4B are fixed to the sheet 5 via the adhesive.

The side portion 52, which is another one of the side portions 51 and 52, is folded inward along the longitudinal direction by the projection 130 of the guide 13 so as to cover the part of the middle portion 50 that remains uncovered with the side portion 51 and also overlay the upper side of the Z-folded portion of the side portion 51, thereby to form the second overhang 32 and the basal wall 30 (see FIG. 6(*d*)).

The standing gather-forming member thus obtained has the first overhang 31 and the second overhang 32 sticking out almost horizontally to both lateral sides of the basal wall 30 so that the upper sides of the first and the second overhangs are in the same plane (the outer surface of the middle portion).

The standing gather-forming member is compressed by the pressing unit 9 to secure the adhesion between the elastic members 4 and the sheet 5 and between the two side portions of the sheet 5. The end of the basal wall 30 is precut and transferred to a sanitary napkin production line.

As described, the apparatus of the present embodiment and the method of making a standing gather-forming member using the apparatus make it possible to continuously and stably produce a standing gather-forming member that will provide a good fit and secure safety against leakage.

In particular, folding the side portions 51 and 52 extending by both sides of the middle portion 50 in a successive manner produces the following effects.

(1) It is easier to control the width of the two overhangs of the standing gathers. For example, the dimension represented by symbol A in FIG. 6(*c*) can be controlled accurately. In other words, the dimension A can be controlled independently by adjusting the guide, etc. The dimension represented by symbol B in FIG. 6(*d*) is also controllable independently.

(2) Processability is improved. For example, since the dimension A shown in FIG. 6(*c*) and the dimension B can be adjusted and controlled independently, the time for adjustment or control for maintenance or during the production can be shortened, which brings about improvement in processability and productivity.

It is preferred that the belts 110 (conveyors) of the first and the second folding units 1A and 1B convey the sheet 5 at the same speed. The conveying speed is preferably 50 to 200 m/min, more preferably 100 to 150 m/min, taking into consideration the fabricability into standing gathers and the stability of various dimensions.

When the sheet 5 is conveyed on the conveyor belts, it is preferred that the middle portion 50 of the sheet 5 make a prescribed angle θ when it enters the area where the overhang is to be formed by the first or the second guides 12 or 13, the angle θ being defined to be the angle between the conveying route R' before entering the area and the conveying route R after entering the area. The angle θ is preferably 100° to 150°, more preferably 135° to 145°, from the standpoint of stable processing.

The vacuum box 112 preferably creates a negative pressure or suction force of 980 to 9800 Pa, more preferably 4900 to 7840 Pa, for securely holding the sheet material and the elastic members.

The sheet S making the standing gathers 3 is preferably of material with a pleasant feel because the gathers 3 are to come into direct contact with the skin. It is also preferred for the material to be hydrophobic to prevent liquid of low surface tension from passing therethrough. As a sheet meeting these requirements, it is recommended to use air-through nonwoven, spun-bonded nonwoven or spunbonded/meltblown composite nonwoven each made of hydrophobic fiber or having been rendered hydrophobic.

In making the standing gathers 3 of nonwoven fabric, it is preferred for the nonwoven fabric to have a bulk softness of 0.03 to 0.3 N, more preferably 0.05 to 0.2 N, measured in the length direction of the gathers and of 0.05 to 0.5 N, more preferably 0.07 to 0.3 N, measured in the width direction (height direction) of the gathers. It is preferred that the bulk softness in the width direction be equal to or higher than that in the length direction. Where the bulk softness values in the length and the width directions and the bulk softness relationship between the length and the width directions meet the above recited preferred conditions, it is easier for the elastic members 4 disposed in the overhangs 31 and 32 to contract in their length direction. Furthermore, the planar seal effect by the overhangs 31 and 32 of the standing gathers 3 and the upright state of the standing gathers 3 are stably maintained irrespective of wearer's movement. The bulk softness in the width direction can be made higher than that in the length direction preferably by, for example, embossing the nonwoven fabric in a wavy pattern across the width.

The bulk softness is measured as follows. A Tensilon tester (RTM-25, supplied by Toyo Baldwin Co., Ltd.) is used for the measurement. A 10 mm by 120 mm piece is cut out of a nonwoven fabric, and the two short sides of the cut piece are joined and stapled at the upper and the lower parts to make a 10 mm high cylindrical specimen. The specimen is compressed in the height direction at a rate of 10 mm/min, and the maximum load is measured as a bulk softness. A bulk softness in the length direction is a value obtained when the compression direction coincides with the length direction of the nonwoven fabric. A bulk softness in the width direction is a value measured with the compression direction coinciding with the width direction of the nonwoven fabric.

Any of various elastic materials conventionally used in sanitary napkins, disposable diapers, etc. can be used as elastic members 4 with no particular limitations. In particular, foamed polyolefins, foamed polyurethane, and natural rubber are of choice.

The form of the elastic members 4 includes a thread, a strip, and a film. Arrangement, extensibility, and/or the number of the elastic members 4 are subject to alteration in accordance with the form of the elastic members and the use of the sanitary napkin.

The elastic members 4 are fixed to the inner side of the sheet 5 in their stretched state. Means for fixing the elastic members 4 include anything that is commonly used in sanitary napkins. Hot melt adhesives and heat sealing are preferred.

The present invention is not limited to the foregoing embodiments, and various modifications can be made therein without departing from the spirit and scope thereof.

While the present invention is especially suited to the production of a member forming standing gathers having a T-shaped cross-section as in the foregoing embodiments, it is applicable to the production of a member forming standing gathers 3' depicted in FIG. 8. FIG. 8 illustrates a sanitary napkin 2' in which the standing gathers 3' have overhangs 31' and 32' that are different in height. This modification is achieved by, for example, as follows. A level difference is made in each of the two belts 110 (as conveyors) of the first and the second folding units 1A and 1B. A sheet 5 is put on the stepped conveyor belt 110 of the first folding unit 1A and conveyed with the level difference transferred to its middle portion 50. A prescribed number of elastic members 4A are arranged in their stretched state on the inner surface of the moving middle portion 50 along the longitudinal direction as shown in FIG. 9(a). As shown in FIG. 9(b), the side portion 51 (one of the side portions extending on both sides of the middle portion 50) is Z-folded by the first guide 12 such that the Z-folded side portion 51 covers the area of the middle portion 50 where the elastic members 4A are disposed thereby to form the first overhang 31'. The sheet 5 having formed the first overhang 31' is then forwarded to the conveying belt 110 of the second folding unit 1B while keeping the level difference as shown in FIG. 9(c). In the second folding unit 1B, the rest of the elastic members, i.e., elastic members 4B, are arranged in the area of the middle portion 50 that remains uncovered with the side portion 51, and the other side portion 52 is folded inward along the longitudinal direction by the second guide 13 to cover the area of the middle portion 50 remaining uncovered by the side portion 51 and also to be superposed on the Z-folded side portion 51. As a result, the second overhang 32' and the basal wall 30' are formed. A standing gatherforming member having the above-described cross-section is also obtained by using apparatus in which only the conveyor belt 110 of the second folding unit 1B has a level difference while the conveyor belt 110 of the first folding unit 1A has a flat (stepless) surface.

In the above-described embodiments, a plurality of elastic members 4 are arranged in each of the first and the second overhangs in their stretched state. Some of the elastic members 4 are arranged on the middle portion in the first step, and the rest of the elastic members are arranged on the middle portion in the second step. Otherwise, it is possible that all the elastic members are disposed on the middle portion 50 in the first step.

As in the foregoing embodiments, folding the side portion 51 in the first folding unit 1A and folding the side portion 52 in the second folding unit 1B are preferably carried out while the middle portion 50 of the sheet 5 is attached to the conveyor belts 110 by the respective suction mechanisms 112 in the first and the second folding units 1A and 1B. Where necessary, suction by the suction mechanisms 112 may be omitted.

While it is preferred that the two overhangs both have the elastic members 4 disposed with equal spacing as in the foregoing embodiments, the elastic members may be disposed in only one of the overhangs 31 and 32 by altering the arrangement of the elastic members 4 in the middle portion 50.

While it is preferred that the superposed areas of the side portions 51 and 52 of the sheet 5 be partly bonded to each other to form the basal wall 30 having the partial joints as in the foregoing embodiments, the bonding of the basal wall 30 may be omitted if desired.

While it is preferred that the adhesive be applied to the elastic members 4 at intervals for fixing the elastic members 4 to the sheet 5 as in the foregoing embodiments, application of the adhesive to the elastic members 4 may be continuous.

Needless to say, the present invention is applicable to the manufacture of not only sanitary napkins but also other absorbent articles including disposable diapers and incontinence pads.

INDUSTRIAL APPLICABILITY

The present invention provides a method and apparatus for making a standing gather-forming member, by which a standing gather-forming member providing a snug fit and a reliable protection against leakage is produced continuously and stably.

The invention claimed is:

1. A method of making a standing gather-forming member having a basal wall and first and second overhangs on both sides of the basal wall, comprising:
   a first step of disposing at least one elastic member in the stretched state on the inner surface of a middle portion of a continuously running strip-shaped sheet along the longitudinal direction of the middle portion and Z-folding one of side portions extending on both longitudinal sides of the middle portion so as to cover a part of the width of the middle portion to form the first overhang and
   a second step of folding the other side portion inward along the longitudinal direction so as to cover the part of the middle portion that remains uncovered with the first-mentioned side portion and also overlay the Z-folded portion of the first-mentioned side portion to form the second overhang and the basal wall,
   the second step following the first step.

2. The method of making a standing gather-forming member according to claim 1, wherein the first and the second overhangs each have one or a plurality of the elastic members disposed in the stretched state, a part of the elastic members are disposed on the middle portion in the first step, and the rest of the elastic members are disposed on the middle portion in the second step.

3. The method of making a standing gather-forming member according to claim 1, further comprising the step, after the first step and before the second step, of applying an adhesive to at least one of the side portions of the sheet to be superposed on each other in the second step.

4. The method of making a standing gather-forming member according to claim 1, wherein the Z-folding of one of the side portions in the first step and the folding of the other side portion in the second step are each carried out while holding the middle portion by suction from the outer surface of the middle portion.

5. The method of making a standing gather-forming member according to claim 1, wherein the sheet is conveyed while forming a level difference in the middle portion thereof.

6. The method of making a standing gather-forming member according to claim 1, wherein the elastic member is fixed by applying an adhesive thereto at intervals.

7. Apparatus for making a standing gather-forming member having a basal wall and first and second overhangs laterally extending from the basal wall,
   the apparatus comprising a conveying system configured to convey along a conveying route a strip-shaped sheet having at least one elastic member disposed in the stretched state on the middle portion thereof, a first folding unit having a first guide provided on one side of the conveying route so as to narrow the width of the conveying route from that side, the first guide having an inwardly projecting projection configured to hang over a part of the middle portion on the conveying route, and a second folding unit having a second guide provided on the other side of the conveying route so as to narrow the width of the conveying route from the other side, the second guide having an inwardly projecting projection configured to hang over a part of the middle portion on the conveying route,
   the projection of the first guide being configured to Z-fold one of side portions extending on both longitudinal sides of the middle portion such that the Z-folded side portion covers a part of the middle portion to form the first overhang, and
   the projection of the second guide being configured to fold the other side portion inward along the longitudinal direction such that the other side portion covers the part of the middle portion that remains uncovered with the first-mentioned side portion and overlays the Z-folded portion of the first-mentioned side portion to form the second overhang and the basal wall.

8. The apparatus for making a standing gather-forming member according to claim 7, further comprising an adhesive applicator between the first guide and the second guide, the adhesive applicator being configured to apply an adhesive to at least one of the side portions being to be superposed on each other in the second folding unit.

9. The apparatus for making a standing gather-forming member according to claim 7, wherein the conveying system comprises air-permeable conveyor belts for conveying the sheet and suction mechanisms configured to attach the middle portion to the belts by suction in the first and the second folding units.

10. The apparatus for making a standing gather-forming member according to claim 7, wherein the conveying system is configured to convey the sheet while making a level difference in the middle portion.

* * * * *